United States Patent

Birch et al.

[11] Patent Number: 6,051,190
[45] Date of Patent: Apr. 18, 2000

[54] METHOD AND APPARATUS FOR TRANSFERRING AND DISPENSING SMALL VOLUMES OF LIQUID AND METHOD FOR MAKING THE APPARATUS

[75] Inventors: William Birch, Samois sur Seine; Alain Carre, Le Chatelet-En-Brie; Eric Francois, Avon, all of France

[73] Assignee: Corning Incorporated, Corning, N.Y.

[21] Appl. No.: 09/059,667

[22] Filed: Apr. 13, 1998

Related U.S. Application Data

[60] Provisional application No. 60/053,971, Jul. 28, 1997.

[30] Foreign Application Priority Data

Jun. 17, 1997 [FR] France .................................. 97 07466

[51] Int. Cl.⁷ .............................. B01L 3/02; G01N 1/12; G01N 35/10
[52] U.S. Cl. ...................... 422/100; 73/864.72; 436/180
[58] Field of Search .................................. 436/180, 809; 422/100, 924, 930; 264/39; 73/864.01, 864.02, 863.32, 864.72

[56] References Cited

U.S. PATENT DOCUMENTS

| | | | |
|---|---|---|---|
| 3,526,132 | 9/1970 | Weintritt | 73/152.04 |
| 3,600,156 | 8/1971 | Clapton et al. | 266/170 X |
| 3,787,378 | 1/1974 | Blank | 264/2.6 X |
| 3,918,034 | 11/1975 | Orth, Jr. | 73/448 |
| 4,085,780 | 4/1978 | Holley | 141/1 |
| 4,339,241 | 7/1982 | Stöcker | 422/104 |
| 4,492,759 | 1/1985 | Gorman et al. | 422/101 X |
| 4,808,402 | 2/1989 | Leibowick et al. | 424/243 |
| 5,133,781 | 7/1992 | De Rosa et al. | 44/300 |
| 5,756,050 | 5/1998 | Ershow et al. | 422/100 |

FOREIGN PATENT DOCUMENTS

| | | |
|---|---|---|
| 641599 | 3/1995 | European Pat. Off. . |
| 120437 | 7/1984 | Japan . |
| 2079069 | 1/1982 | United Kingdom . |
| 9872 | 5/1993 | WIPO . |
| 4594 | 2/1995 | WIPO . |

Primary Examiner—Thomas P. Noland
Attorney, Agent, or Firm—Thomas R. Beall

[57] ABSTRACT

The invention relates to the transfer and distribution, notably in a biological or chemical analysis, of a small amount of liquid. The invention relates notably to a method which consists of providing a transfer tool (18) having at least one rod (10) whose lower surface (12) of pre-determined cross section is wettable and of which at least one side surface (14) is non-wettable; immersing the rod (10) into a reservoir containing a liquid, for a pre-determined period of time and at a pre-determined depth; removing the rod (10) from the reservoir so that a liquid drop is retained on the lower surface (12) of the rod (10); positioning the rod (10) over a receptor medium; and placing the drop in contact with a surface of a receptor medium. The invention also relates to the transfer tool (18) which has in its structure at least one rod (10) and to a method for making the transfer tool (18).

2 Claims, 6 Drawing Sheets

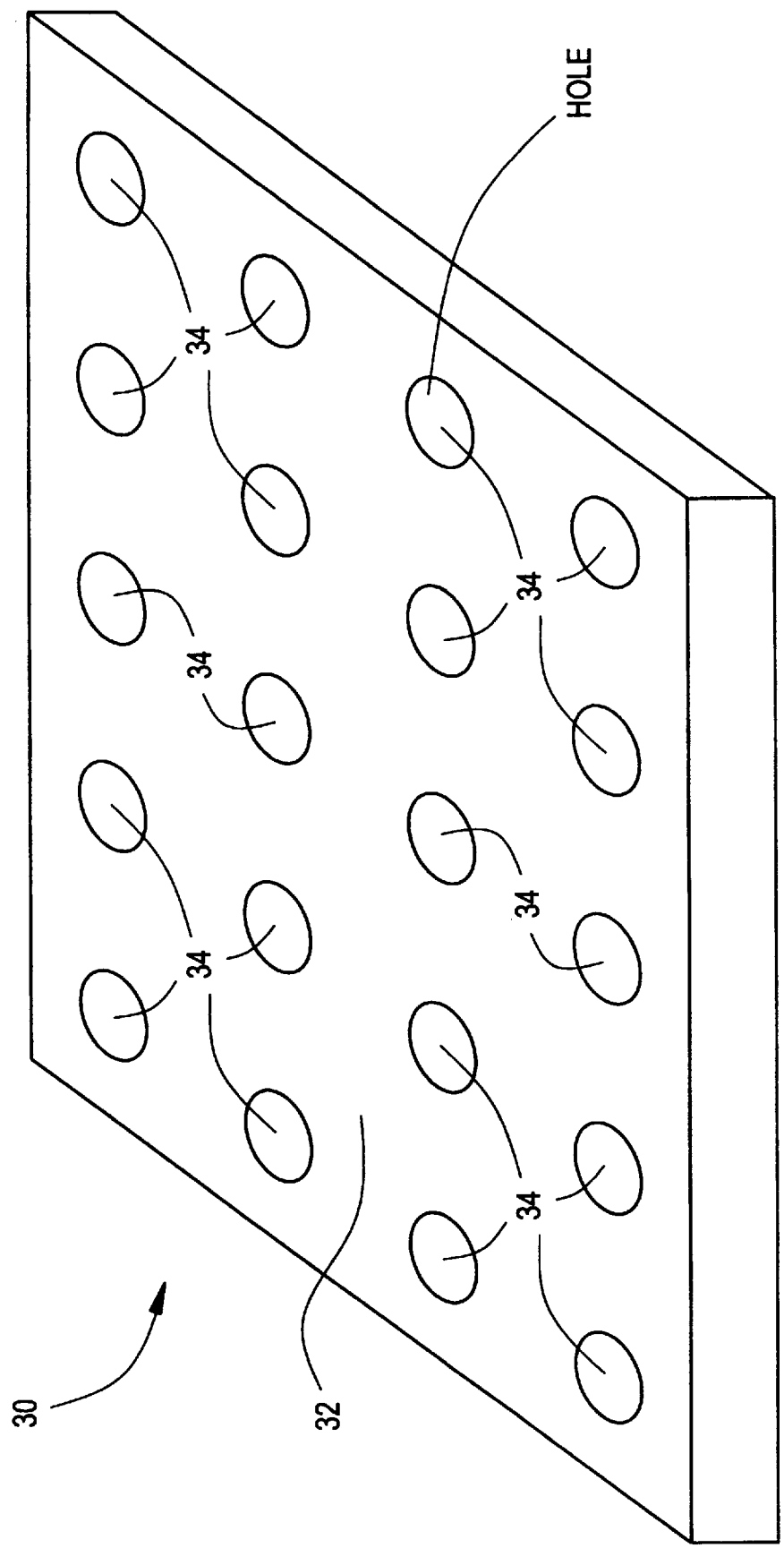

HOLE AND PIN PLATE DIAMETER
MOLD THICKNESS AND PIN HEIGHT

ADHESIVE TAPE CLOSING ONE END OF THE MOLD

WETTING TREATMENT

WET PIN TOP — DEWET PIN SIDE WALL

6,051,190

METHOD AND APPARATUS FOR TRANSFERRING AND DISPENSING SMALL VOLUMES OF LIQUID AND METHOD FOR MAKING THE APPARATUS

This application claims the benefit of French Application number FR 97 07466, filed Jun. 6, 1997 and U.S. Provisional applications Ser. No. 60/053,971, filed Jul. 28, 1997.

FIELD OF THE INVENTION

The present invention relates to a method and apparatus for the transfer and dispensing small volumes of liquid, especially appropriate in the contexts of biological or chemical analyses and to a method for making the apparatus.

BACKGROUND OF THE INVENTION

During the execution of tests or cultures on biological molecules or cell cultures, plates formed from molded thermoplastic material, e.g. polycarbonate or polystyrene, are usually used today. Usually, the multi-well plate which is used has dimensions of about 80×125 mm, and the wells have a diameter of about 8 mm. These dimensions are normalized in industry due to the large variety of apparatuses, which have been developed for automatic analyses. The wells of these plates are often filled with a collection of pipettes, which are displaced manually or by robotized device. The samples of the products formed in the wells are collected, for example with the aid of a collection of needles, of stainless steel or the tips of plastic material, which are immersed in the wells.

Given that it is desirable to carry out a large number of analyses on a single plate, the use of plates having an increasingly large number of wells per plate is growing. An increasingly large number of wells on the same standardized plate gives wells of very small volume, thereby it is then necessary to have tools at one's disposal which enable dispensing small volumes of liquid. Many devices exist for dispensing liquids in small doses ranging from volumes of one milliliter to fractions of a milliliter. Current developments bearing on multi-well plates include progress relating to micro-well and micro-plate technology, it being possible for example to have up to 10,000 wells per square centimeter (see especially U.S. Ser. No. 08/747,425). These wells are separated by a distance of about 100 $\mu$m, each well having a depth of 15 to 30 $\mu$m and a diameter of 20 to 50 $\mu$m. In order to perform tests with the aid of these micro-plates, it is necessary to be able to carry out accurate transfers of liquid volumes ranging from a thousandth to a millionth of a cubic millimeter; transfers to and from such micro-wells. Classical micro-syringes are unable to manipulate such small volumes; thereby it is necessary to make liquid handling apparatuses, which are conceived in a radically novel manner.

A tool is currently on sale, which comprises a matrix of stainless steel pins arranged so that each pin is aligned on a well from a 96-well plate. A drop attaches to an individual pin under the action of the forces of surface tension and can then be transferred. The tool has 30 precision grooves cut into the pins, near to their tip, for determining the volume dispensed. These pins are advertised as capable of dispensing volumes of 1 mm$^3$ and larger to wells or membrane surfaces.

Micro-syringes use a liquid reservoir comprising a capillary tube (or liquid chamber) and a piston for dispensing the liquid by pushing it out through a needle. Such a system is not suited to the delivery of liquid volumes in the order of a thousandth to a millionth of a cubic millimeter.

It would be desirable to have a method at one's disposal for transferring and dispensing volumes in the order of a thousandth to a millionth of a cubic millimeter into micro-wells of a micro-plate with a good reproducibility. (It is recalled here, in order to facilitate reading the present text, that 1 mm$^3$=1 $\mu$l=10$^{-6}$l). The invention relates to such a method of transferring and depositing a drop, notably of biological material or of a reagent, onto a surface or into a well or a depression as well as the tool associated with said method.

It would also be desirable to have a method for making a tool for transferring and dispensing volumes in the order of a thousandth to a millionth of a cubic millimeter into micro-wells of a micro-plate. The invention relates to such a method of making a tool for transferring and depositing a drop, notably of biological material or of a reagent, onto a surface or into a well or a depression as well as the tool resulting from the method.

SUMMARY OF THE INVENTION

The present invention uses the tip of a solid fiber or rod, for depositing microscopic drops having volumes between a thousandth and a millionth of a cubic millimeter. The use of a rod or fiber having controlled wetting and non-wetting properties allows a simple delivery of precisely controlled liquid volumes from a few cubic millimeters to a millionth of a cubic millimeter and less. The Applicant has found that, in the case of a non-wettable rod, which has a wettable tip, the volume of a liquid drop formed by dipping the rod into a liquid reservoir is constant and reproducible. The volume of the drop can be controlled by the size of the cross section of the lower surface of the rod. The larger this size, the larger the volume of the drop that can be suspended from the tip is. A small supplementary control of the volume of liquid deposited on the pin can be obtained by varying the depth; the speed of immersion and/or removal of said pin. The diameter of the cross section of the lower surface of the rod (diameter of the rod, in the hypothesis of a cylindrical rod) is preferably less than the capillary length of the liquid or in the order of this length. Drops smaller than a cubic millimeter, made with a cross sectional diameter of the lower surface of the rod much smaller than the capillary length of the liquid do not experience significant influences due to gravity.

The object therefore of the present invention is a liquid transfer tool which enables delivering a liquid volume of a few cubic millimeters to less than a cubic millimeter into a well or onto a substrate surface (to said transfer is therefore generally associated the distribution of the liquid, but this association is not however inescapable. The drop taken can be dried on the tip of the rod for analysis ends: see later); said transfer tool characteristically comprises:

at least one rod having a wettable tip of pre-determined cross section and at least one non-wettable side; and
  a support structure for said rod.

Said rod advantageously has its wettable extremity or tip and its non-wettable side(s). Advantageously, this is a rod of constant cross section, notably a rod in the form of a cylinder; the radius of its circular cross section generally being between 2 mm and 1 $\mu$m with the result that the diameter of said circular cross section is less than or equal to the capillary length of the liquid.

According to preferred embodiments:

said tool of the present invention has several rods whose arrangement and separation are such that they are aligned on the wells distributed on a plate of several wells;

its rod(s) is(are) in metal, ceramic, glass, polymer or in a composite material;

the tip of its rod(s) is hydrophilic and the side surface of said rod(s) is hydrophobic or the tip of its rod(s) is oleophilic and the side surface of said rod(s) is oleophobic;

the tip of its rod(s) is coated with a material, which does not adhere biological materials.

Another object of the present invention is the use of said transfer tool, namely methods of transfer and distribution of small liquid volumes (of a few cubic millimeters to less than a cubic millimeter) according to which:

a transfer tool is at one's disposal which has at least one rod whose lower surface of predetermined cross section is wettable and of which at least one side surface is non-wettable;

said rod is immersed into a liquid-containing reservoir for a pre-determined period of time and at a pre-determined depth;

said rod is removed from said reservoir so that a drop of liquid is retained on the lower surface of said rod;

said rod is positioned above a receptor medium; and the drop is placed in contact with the surface of said receptor medium; (context of the deposit of the liquid in a receptor medium; or a transfer tool is at one's disposal which has at least one rod whose lower surface of pre-determined cross section is wettable and of which at least one side surface is non-wettable;

said rod is immersed into the well (of a multi-well plate) which contains the liquid for a pre-determined period of time and at a pre-determined depth;

said rod is removed from said well so that a liquid drop is retained on the lower surface of the rod;

said rod is positioned over a receptor container; and the drip is placed in contact with said receptor container; (context of liquid removal from a well of a multi-well plate).

It will already have been understood that in the first context, the receptor medium is advantageously a multi-well plate and that therefore, within this context, the removed drop is advantageously placed in contact with an internal surface of a well of said multi-well plate. Said internal surface of said well is advantageously wettable.

In the second context, within the context of an implementation variant, there is also the internal surface of the well, which is wettable.

Generally, in one or the other of said contexts, the method is advantageously implemented:

with a transfer tool having several rods, arranged and separated so that they are aligned on the wells distributed on a multi-well plate;

under the conditions below:

the depth of immersion of said rod is at least equal to twice the diameter of the circular cross section of the lower surface of said rod;

the period of time of immersion of said rod corresponds to a period which is sufficient to allow the liquid to attain an equilibrium configuration or almost equilibrium at the lower surface (the maximum of liquid is thus taken);

said rod is cylindrical and the radius of its circular cross section is between 2 mm and 1 $\mu$m;

the lower surface of the rod is hydrophilic and the side surface of said rod is hydrophobic or the lower surface of the rod is oleophilic and the side surface of said rod is oleophobic.

The tools and method of the invention are particularly efficient in ensuring the transfer of amounts of liquid whose volume is less than about 2 $mm^3$.

Yet another object of the present invention is the method of making a transfer tool for the transfer and distribution of small liquid volumes (of a few cubic millimeters to less than a cubic millimeter);

Other characteristics and advantages of the invention shall be better understood upon reading the following description of implementation examples, made with reference to the annexed drawings in which:

BRIEF DESCRIPTION OF THE FIGURES

FIG. 7 is a perspective view of a mold for use in the manufacture of a transfer tool according to the invention;

DETAILED DESCRIPTION OF THE INVENTION

The method according to the present invention is based on the use of one or more rods. The term "rod" means any glass, metal, polymer, ceramic or composite material having the shape of a pin, rod or fiber. Generally, such a rod is cylindrical and has a circular cross section of constant radius R. It is, however, in no way excluded from the context of the invention that said rod has a non-circular cross section (oval, polygonal, . . . ) and/or a variable cross section according to its height. The glass or composite material rods are treated so that they are non-wettable by the liquid transferred. For example, when a water-based liquid is being transferred, the outer surface of the rods is treated so that it becomes hydrophobic. When an organic solvent or other oil-based liquid is being transferred, the outer surface of the rod is treated so that it becomes oleophobic, unless the material is such that its surface is already oleophobic. In this case, no surface treatment of the rod is necessary.

Figure 1:
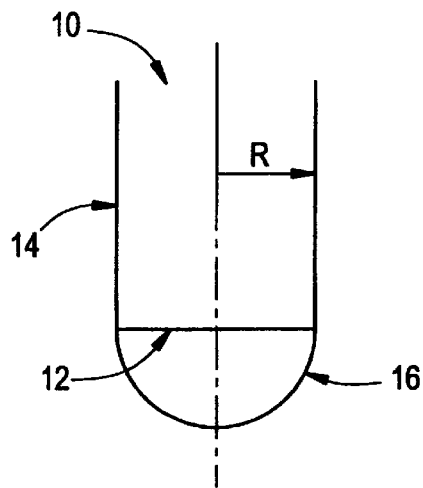
FIG. 1 is a cross-sectional view of a pin according to the invention and a liquid drop, which is attached to it.

FIG. 1 shows the tip of a rod 10 according to the invention, in cross section. The rod 10 has a wettable tip 12 and non-wettable sides 14. A liquid drop 16 is attached to the wettable tip 12. The wettable tip or lower surface 12 is hydrophilic.

The non-wetting characteristic of the sides of the rod and the wetting characteristic of the tip may be obtained in a variety of ways and by employing many different techniques. Some of the techniques are the following: 1) coating an entire rod and cleaving the rod, 2) coating the entire rod and polishing or abrading its end, 3) coating the entire rod, cutting or polishing the end, and applying a coating to the exposed tip with the aid of a stamp, or by contacting the exposed tip to a surface coating on a substrate, 4) cutting or polishing the end of a rod, contacting said end with a thin polymer film or other non-permeable film or substrate, and coating the sides of the rod by the required hydrophobic or oleophobic treatment, and 5) simply cutting, polishing, abrading, or coating the tip of a rod that intrinsically possesses the desired or required hydrophobic or oleophobic properties.

As a non-limiting example, the non-wetting treatment may consist of a coating of a glass rod. The coating can be deposited by dipping a clean rod in a solution of perflourodecyltrichlorosilane in an organic solvent. One liter of solution is obtained by mixing 2 cm$^3$ of perfluorodecyltrichlorosilane in a mixture of 700 cm$^3$ of dried kerosene and 300 cm$^3$ of dichloromethane. The resulting coating has a very low surface energy and is non-wetted by most liquids. Another simple process of coating the glass with perfluorosilanes such as perfluorodecyltrichlorosilane consists of exposing the glass to the vapor of the silane. Following this treatment, the tip of the rod is cut or separated in order to expose a pristine, untreated lower surface at its tip. This untreated lower surface can be wetted, while the sides of the rod remain coated and thereby, non-wettable. When the rod is immersed into a liquid reservoir, only its tip is wettable by the liquid. As the rod is pulled out of the reservoir, a semi-spherical cap (drop) of liquid is attached by surface tension, only to the wettable surface that has been exposed, as shown in FIG. 1.

The volume of the liquid collected at the tip of the rod is reproducible and depends little on the depth of immersion of the rod into the reservoir, provided that the rod is withdrawn from the liquid slowly enough to allow the liquid to flow and to wet the tip of the rod. The volume of the drop of liquid attached to the wettable tip $V_i$ is essentially a function of the radius of the rod, R. As long as the depth of the liquid reservoir is several times greater than the diameter of the rod (at least equal o twice said diameter), the volume of liquid collected at the rod tip is independent of the depth of the liquid reservoir.

When the liquid drop is transferred to a receiving material having a solid surface, such as a multi-well plate or a flat surface, and when the drop is in contact with the surface of the receiving material, approximately 50% of the volume of the drop is transferred to the solid surface, leaving 50% of volume $V_i$ on the tip of the rod.

The volume of a given liquid transferred by a pin of given size onto a given uniform flat wettable surface at a given speed, with the pin perpendicular to the surface and coming into contact with the surface is constant in the absence of thermal or mechanical fluctuations. The fraction of liquid transferred from a pin having a wettable tip onto a wettable surface is approximately 50%. This value may vary up to ±10% if the pin is not in full contact with the surface, if the contact speed is increased, or if the wetting properties of the receiving surface vary slightly.

Surfaces that show reproducible volume transfers using these techniques include glasses, ceramics, metals and polymers, with the exception of most silicones and fluoropolymers. In the case of surfaces that are not wetted by the liquid, the transfer ratio drops to about 10%, or less. It should be noted that transfers of liquid onto non-wettable surfaces can be performed, but the liquid volume transfer is significantly less than with transfers onto wettable surfaces.

The present invention relates to a device intended for transferring liquid volumes between a thousandth and a millionth of a cubic millimeter, with accurate control.

Figures 4A, 4B, 4C, 4D, 4E:
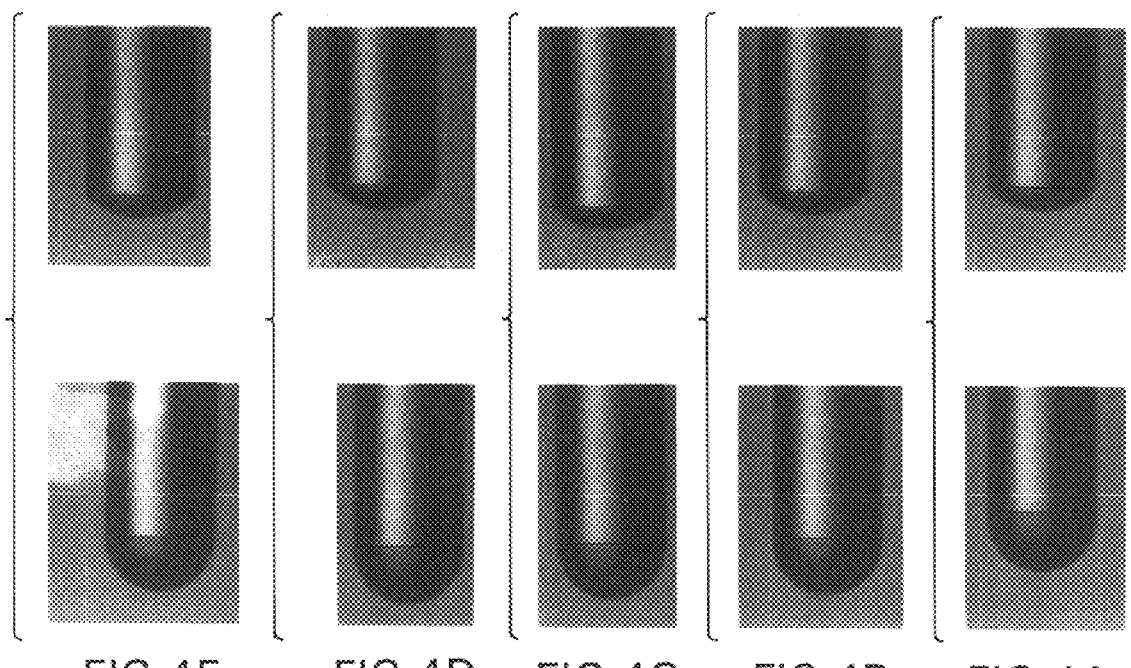
FIG. 4 represents a series of photographs of the same pin, before and after 5 successive distributions of liquid.

FIG. 4 represents a series of photographs of a glass rod with a diameter of 125 μm (radius of 62.5 μm) before and after 5 consecutive transfers 1, 2, 3, 4, 5. A volume of 0.24·10$^{-3}$ mm$^3$ of tricresylphosphate was accurately transferred to a solid surface of polyethylene terephthalate each time. Upon considering said FIG. 4, it is seen that the method of the invention is perfectly reproducible and that about half of the drop transferred has been deposited each time.

The Table below indicates the approximate radius R of the rod, for a transfer of a given $V_m$, onto a flat surface or onto a micro-well on a multi-well plate. Two solid surfaces are considered, one moderately or highly wettable, labeled $V_m$ (A), and the other which is not wetted by the liquid, for example formed from a silicone or flouropolymer, labeled $V_m$ (B).

| R | 1 mm | 0.43 mm | 0.20 mm | 0.09 mm | 60 μm | 43 μm | 20 μm | 9.3 μm |
|---|---|---|---|---|---|---|---|---|
| $V_m$ (A) | 1.0 μl | 0.08 μl | 8 nl | 0.7 nl | 0.2 nl | 0.08 nl | 8 pl | 0.8 pl |
| $V_m$ (B) | 100 nl | 8 nl | 0.8 nl | 73 pl | 22 pl | 8 pl | 0.8 pl | 0.08 pl |

It may be noted that by varying the rod radius within the range of 1 mm–9.3 μm, a transfer of any volume may be made onto a wettable surface for all volumes between 1.0 mm$^3$ and 0.8·10$^{-6}$ mm$^3$ (between 1 μm and 0.8 pl). The table is a guide, which enables determining liquid volumes transferred by the device specified according to the invention.

Figure 5:
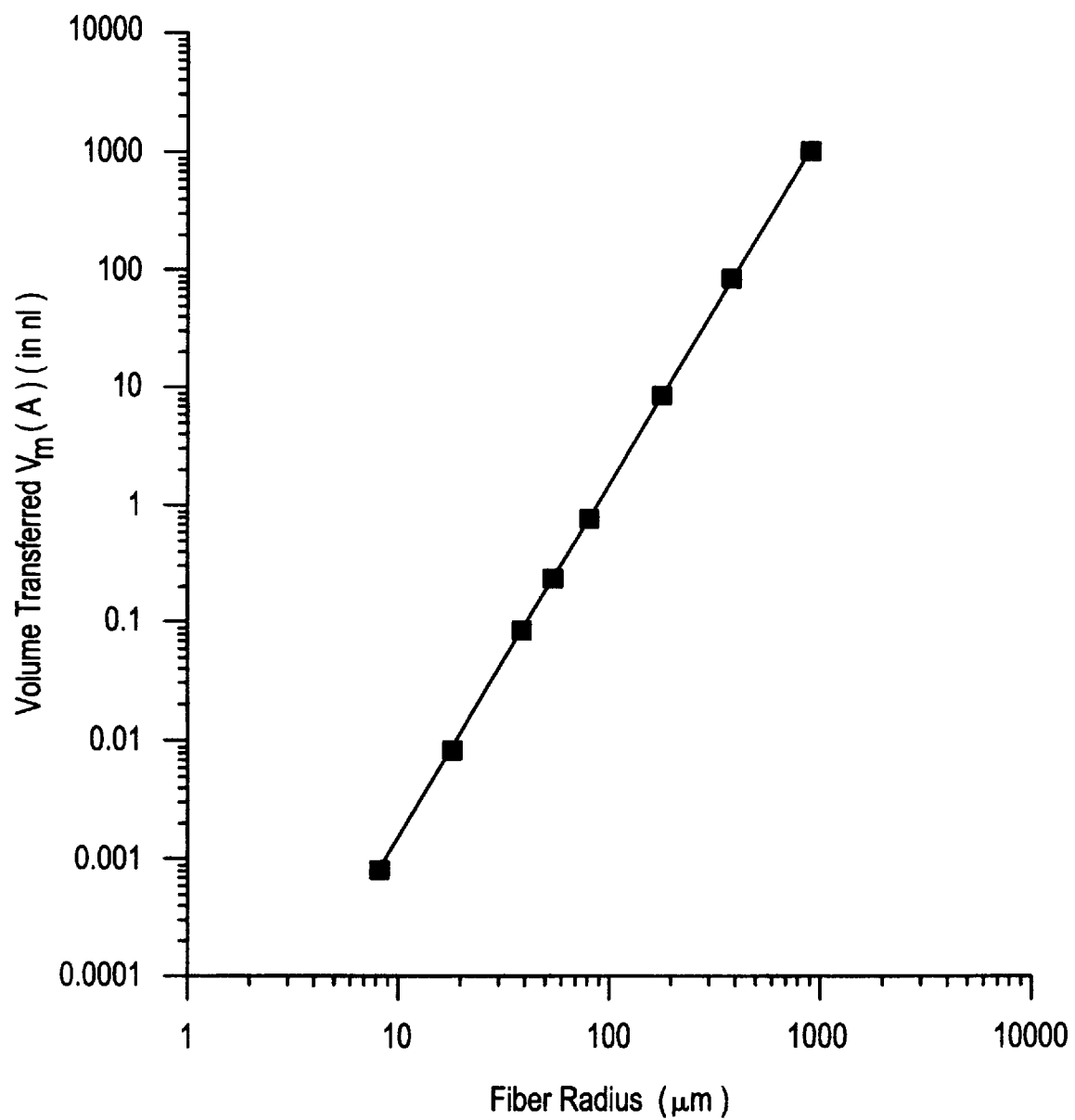
FIG. 5 is a graph, which indicates the variation of the volume distributed onto a wettable surface as a function of the radius of the rod, in the case of a transfer rod according to the invention.

Further, FIG. 5 shows that the relationship between rod radius and volume transferred $V_m$ (A), is logarithmically linear. The line is plotted from the results in the Table. Thus, one needs only to consult FIG. 5 in order to determine the appropriate rod radius for a desired volume transfer. For larger volumes above 1.0 mm$^3$, it is necessary that the diameter of the rod be increased.

Figure 6:
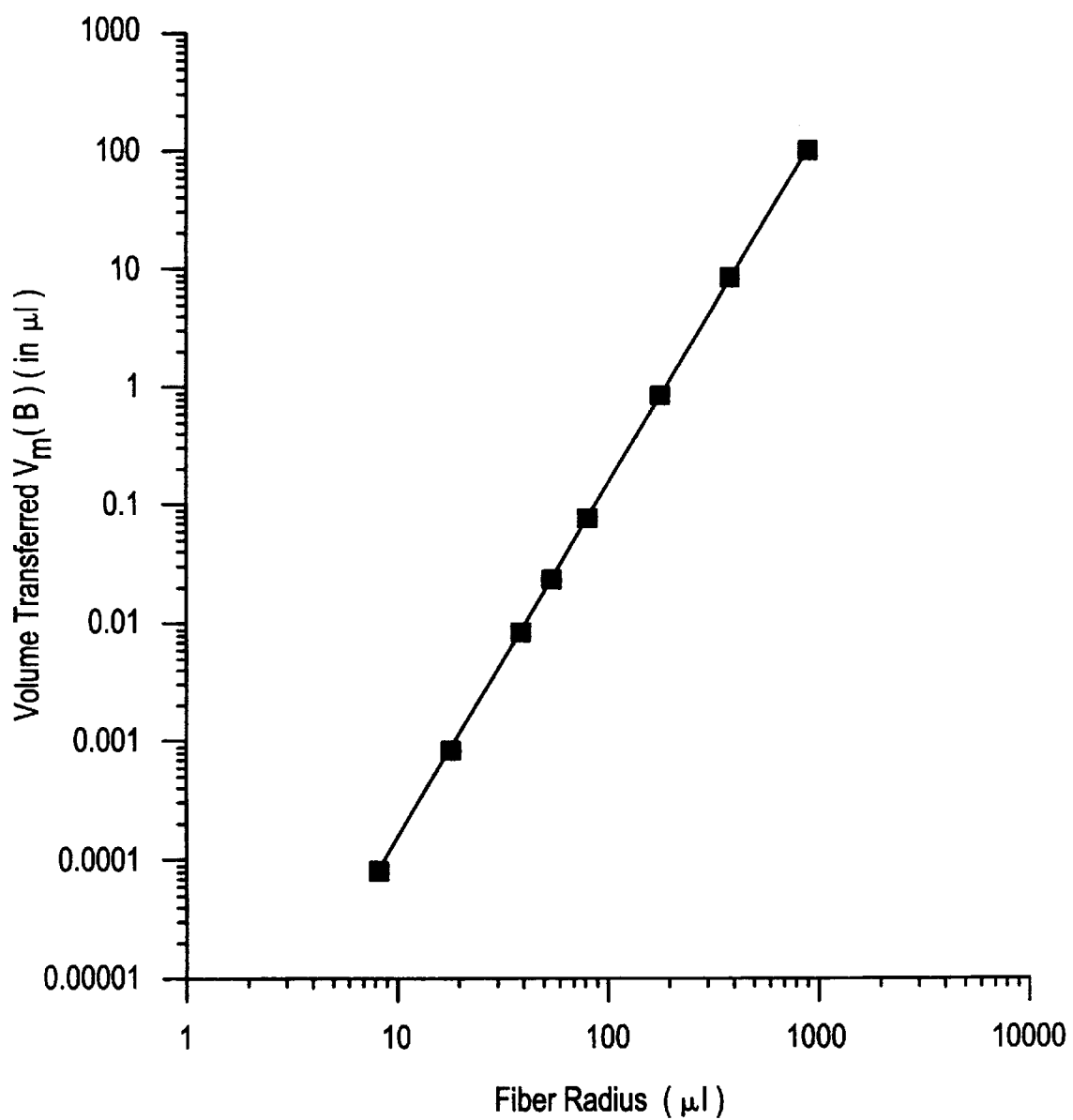
FIG. 6 is a graph indicating the variation of the volume distributed onto a non-wettable surface as a function of the radius of the rod in the case of a transfer rod according to the invention.

FIG. 6 represents the relationship between the rod radius and the volume transferred $V_m$(B) when transferring t a non-wettable surface. As in FIG. 5, the relationship is still linear when plotted on logarithmic scale.

It should be noted that $V_m$ may vary slightly with the surface tension of the liquid and its viscosity. Some calibration of the device may therefore be required for the delivery of accurate volumes of a given liquid.

It should be remembered hereby that the transfer device is not limited to cylindrical rods. The rods may have any cross sectional shape including rectangles or squares. Rods without sharp corners, for example of circular or oval cross section, are preferred since they have been found to give the best volume reproducibility. The rods do not however have to have a cross section, which is constant throughout all their height.

Further, in order to dispense a large volume of liquid, or in order that a given surface be covered, multiple pins forming a matrix may also be used.

Figure 2:
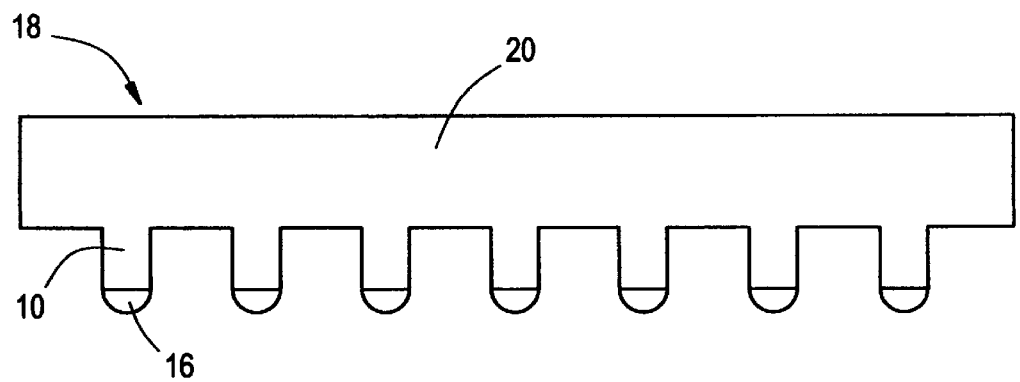
FIG. 2 is a cross-sectional view of a transfer and dispensing tool of the invention, that may be used in implementing the method of the invention.
Figure 3:
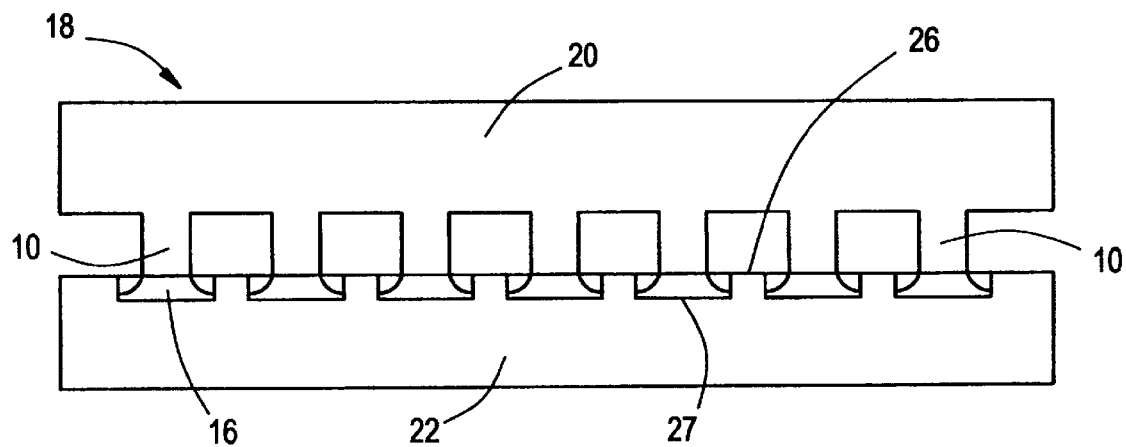
FIG. 3 is a cross-sectional view of a transfer tool which is in contact with a multi-well plate and which deposits liquid drop into the wells.

With the addition of simply engineered support devices, a matrix comprising multiple and parallel rods may be created for the transferring matrices of drops into micro-well plate structures. Preferably, the matrix comprises several rods arranged and separated so that they are aligned with a collection of wells distributed in a multi-well plate. FIG. 2 represents the cross section of a liquid transfer tool 18 having a matrix of rods 10 which project downwards from a support 20. Each rod 10 carries a drop of liquid 16. FIG. 3 represents the transfer tool 18 lowered over a plate 22 having wells 24. Each rod 10 is aligned with a corresponding well 24. Preferably, the interior of the wells 24 are wettable and the upper surface 26 of the plate 22 is non-wettable. In this way, the drop 16 will be drawn exclusively into a corresponding well 24 and there will be no spill-over onto the surface of the plate. The tool 18 is lowered to the point where each drop 16 is in contact with the interior of each corresponding well 24. Approximately 50% of the volume of the drop is deposited into the well. The same process may also be employed in reverse (not shown). Empty rods from a transfer tool are lowered into liquid containing wells of a multi-well plate. Each rod of the tool is immersed in the liquid of a corresponding well. Drops are attached to the wettable surface of each rod tip as the rods are removed from the well. The liquid drops are then placed in contact with the surface of a receiving container, for example a second multi-well plate, and approximately 50% of the volume of each drop is deposited.

It is possible to obtain similar results to those described above by taking a rod that is non-wettable and applying a wettable coating to the tip of the rod and the lower parts of the side walls. In this way, rods of the same diameter may be able to carry different volumes of liquid, simply as a function of the height of application of the wettable coating up the side walls of the rod. The coating may be applied by dipping the rod a certain distance into a solution containing a molecular species to be deposited for example. It is noted hereby that said height of application of said coating is not important. In any case, rods of this type and their uses make an integral part of the context of the present invention.

It should be noted that the use of a transfer as described above can extend to other applications. For example, the volumetrically quantifiable drop at the tip of the rod can be used in a variety of quantitative analysis procedures. The drop can be dried and testing can be performed on the residue left on the wettable tip. Examples of known tests that can be performed on this residue include NMR, mass spectrophotometry, micro FTIR, time of flight, and matrix assisted laser absorption. Testing residue from the tip of a pin or rod is known, but one advantage of using a glass rod as a substrate for the residue, for example, is the lack of background carbon.

Further, the transfer tool may be used to deliver known volumes of liquid into a miniaturized diagnostic testing apparatus such as that described in European Patent Application EP-A-381 501 (filed under the No. 90 301 061.9).

Additionally, the rod tip may advantageously be coated with a coating, which does not adhere biological molecules, based, for example, on polyethylene oxide or polyacrylamide. This type of coating serves to prevent the adsorption of biological materials such as peptides, proteins, nucleic acids, or cells to the rod tip surface.

Another embodiment of the present invention is a product having a single pin having non-wettable sides and a wettable tip held in a pen-like structural support. The pipette structure can be held in a user's hand. In the same fashion as with a mechanical pencil, a pin is extended from the support structure by a control lever on the top of the pipette. After the pin is extended, a cutting edge makes a fresh cut of the pin tip, leaving a fresh exposed wettable surface. In this way, a user can make a single transfer, cut and eject the used tip and have a fresh tip ready for subsequent transfers. Ideally, such a device is employed for transfers of liquid in an amount less than or equal to 2 $mm^3$, but could be extended to larger volumes. The length of the pin ideally should be sufficient to reach the bottom of a 96-well plate or centrifuge tubes.

A further embodiment of the hand held pipetter is a pen-like support structure having a magazine of pins of various diameters and having wettable tips, which are dispensed and ejected with an index finer-controlled stopper. Each volume determination pin is preferably color coded, ring coded, or size coded based on the volume of liquid which can be transferred.

A further embodiment of the hand held pipetter is a pen-like support structure capable of picking up pins from a rack and subsequently ejecting them with the aid of a finger lever after use.

The hand pipette system described can extend to a matrix or row of pins (therefore comprising more than one pipette).

With reference to FIGS. 8A–8E, one method for making a liquid handling and transfer tool for mini or micro-well plates according to the invention is discussed below:

First, the material used to make the tool is mixed. In this particular embodiment, the material is a two component silicone rubber, which is intrinsically non-wettable due to its low surface tension ($\cong 20$ mN·$m^{-1}$), although any type of intrinsically non-wettable material could be used. In this particular example, the silicone rubber used is SYLGARD 184 from BASF which is mixed with a curing agent in the ration of 10 parts in weight of the curing agent for 100 parts of liquid polymer. Other examples of silicone rubber candidates include SYLGARD 182 from BASF or RTV 630 or 615 from General Electric Co.

Next, the mold 30 for making the tool 20 is provided as illustrated in FIGS. 7 and 8A–8D. The mold 30 is a plate 32 with a plurality of holes 34 which extend through the plate from one surface 36 to the other opposing surface 38 of the plate 32. The diameter of each hole 34 is equal to the desired diameter of pins and the thickness of the plate 32 is equal to the required height of pins to prevent flooding of the rubber tool when the liquid is applied. The placement of the holes 34 in the mold 30 corresponds to the placement of the wells in the mini or micro-well plate. In this particular embodiment, the mold 30 is metallic although the mold 30 could be made out of other materials.

Figure 8A:
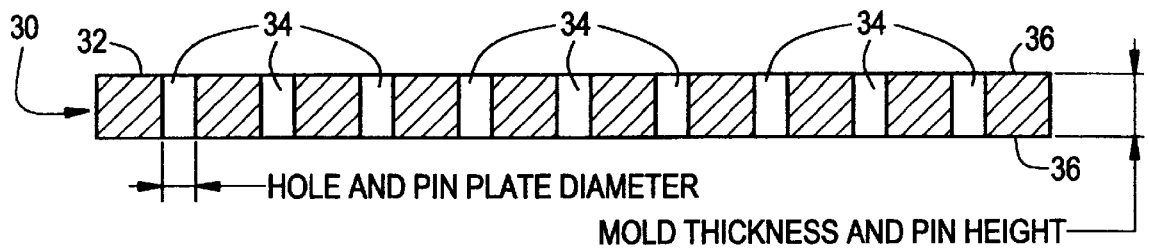
FIG. 8A is a cross-sectional view of the mold for use in the manufacture of a transfer tool according to the invention.
Figure 8B:
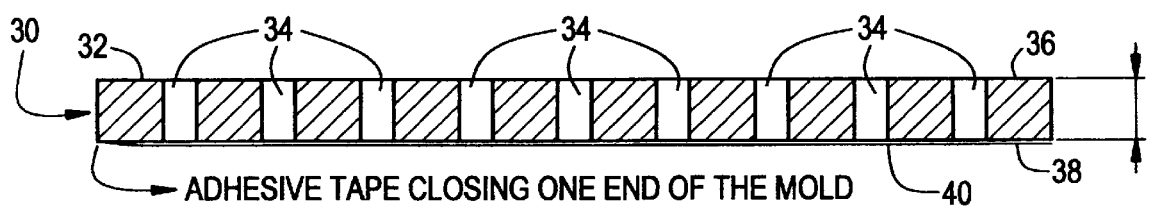
FIG. 8B is a cross-sectional view of the mold shown in FIG. 7A with the removable cover attached to one surface of the mold.

Next, one face 38 of the mold 30 is temporarily covered with a removable cover 40 as shown in FIG. 8B. In this particular embodiment, an adhesive tape is used to cover the holes 34 on one surface 38, although other materials to temporarily cover the holes 34 could be used.

Figure 8C:
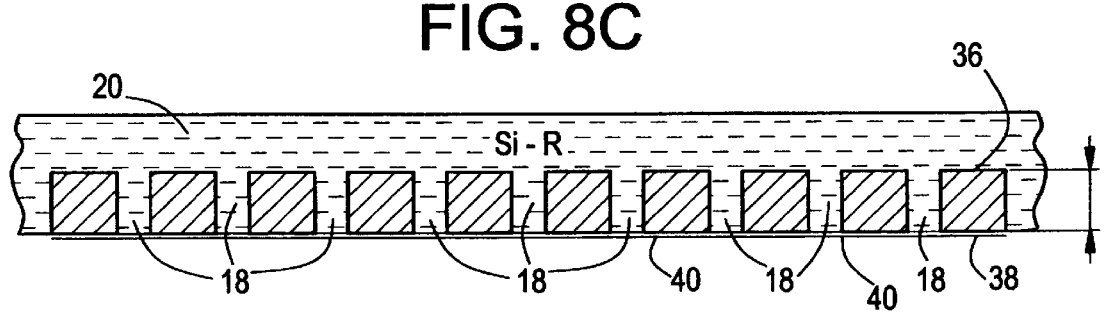
FIG. 8C is a cross-sectional view of the mold shown in FIG. 7B filled with an intrinsically non-wettable material to form the transfer tool.

Once the holes 34 on one face 38 of the plate 32 are blocked, then the material, in this particular example silicone rubber, is poured into the mold 30 as shown in FIG. 8C.

Figure 8D:
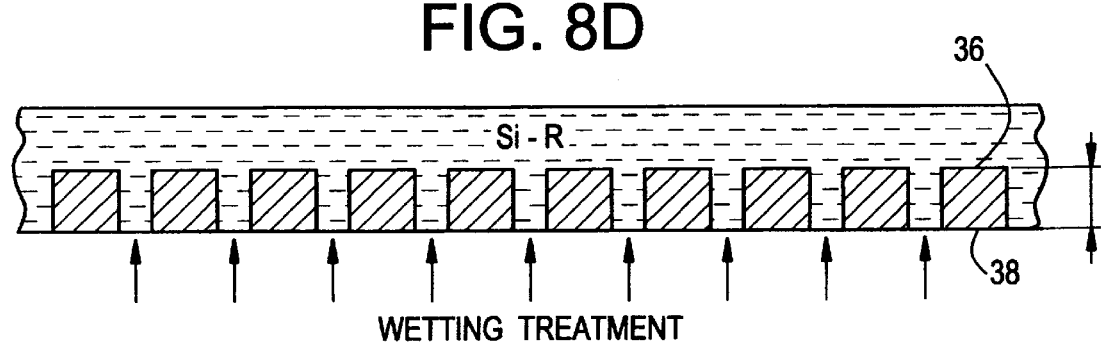
FIG. 8D is a cross-sectional view of the mold filled with the intrinsically non-wettable material with the cover removed.

The material is then allowed to set for a period of time at room temperature, typically ranging between 15 and ^60 hours. In this particular embodiment, the rubber is cured at room temperature, e.g., at about 20° C. to 25° C., overnight and is then post-cured at 100° C. for 1 hour. After the material is cured, the removable cover 40 is taken off the mold 30 which exposes the drop surface of the rods or pins 18 for the tool 20 as shown in FIG. 8D. The removable cover 40 may also be removed before the rubber is post cured at 100° C. for 1 hour.

The exposed top surface or tips of rods 18 the tool 20 are then treated chemically or physically, in order to develop wetting properties. Since the other parts of the tool 20 are still in contact with the mold 30, this treatment does not effect those surfaces. By way of example, the top surface of the pins 18 can be exposed to the action of an oxygen plasma followed by a chemical grafting of a polar material like silica to develop wetting properties.

Figure 8E:
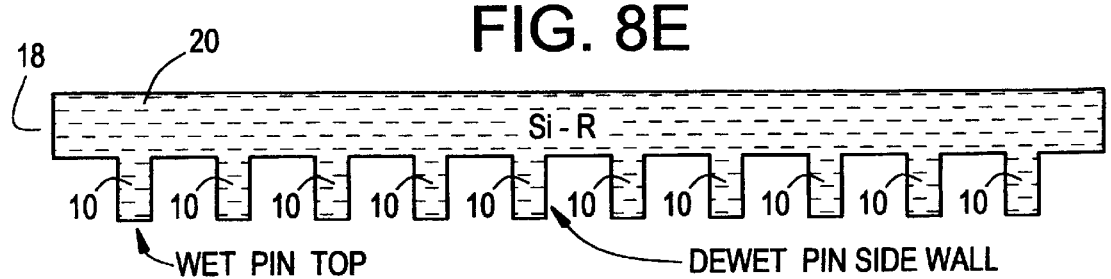
FIG. 8E is a cross-sectional view of the resulting transfer tool.

Once the top surface of the rods 18 have been treated, the tool 20 is removed from the mold 30 and is ready from use as shown in FIG. 8E. If manufactured properly, the top surface of the rods 18 should be wettable and the remainder of the tool 20 should be non-wettable.

One illustrative and non-limiting example of the process of producing a liquid transfer tool according to the invention is described below:

In this particular example, a rubber transfer tool for a well plate (75×110 mm$^2$) which has 384 wells, each well having a diameter of 1.8 mm, was made. To make this tool, first a stainless steel plate 1.8 mm thick having 384 holes of 1.8 mm of diameter is needed. Next, one face of the metal plate is blocked with an adhesive paper.

Meanwhile, the silicone rubber used to make the tool 20 in this particular example is prepared from about 70 g of polymerizable SYLGARD 184 mixture (liquid polymer and curing agent). Once the silicone rubber is prepared, the silicon rubber is poured into the plate. The silicon rubber is left to cure overnight at room temperature. In the morning, the adhesive paper is peeled off from the mold and the silicone is post-cured for 1 hour at 100° C.

Next, the pin tops of the rubber tool were treated to make them wettable. Before unmolding, the pin top of the rubber tool is exposed for 1 minute to the action of an oxygen plasma (power=100 W, p $O_2$=0.2 torr, gas flow rate=50 cm$^3$·min$^{-1}$). After the plasma treatment, the rubber (still in its mold) was dipped into a solution of tetramethoxysilane in an acidified mixture of water and ethanol to obtain the hydrolysis of the silane. To obtain 1 liter of silane solution, 100 g tetramethoxysilane were mixed with 100 g of ethanol and 50 g of water acidified with 0.3 g HCl 12N. This solution was diluted after 1 hour with 570 g of ethanol. After dipping the rubber tool in its mold overnight, the rubber in its mold was rinsed with deionized water and then dried under air flow. This treatment rendered the pin tops of the rubber transfer tool wettable. After the described surface treatments of pin tops, the rubber tool was unmolded and ready for use.

Very simple transfer experiments with a water based solution demonstrate that the transfer tool make according to this method works as expected, liquid droplets of equal volume being formed on pin tops, the liquid not wetting the pin walls. The process described can be adapted to mold different transfer tools with other silicone rubbery materials.

Of course, various modifications maybe make by the person skilled in the art to the methods and apparatuses, which have just been described only as a non-limiting example, without leaving the context of the invention.

What is claimed is:

1. A liquid dispensing apparatus for use in biological or chemical assays comprising:

at least one rod having a radius ranging from approximately 2 mm–1 μm and having a hydrophilic wetting tip and at least one oleophobic non-wetting side, said at least one rod having a diameter less than or equal to the capillary length of said liquid, a support structure holding said at least one rod, and whereby said at least one rod delivers a sub-microliter volume of liquid to a receiving medium.

2. A liquid dispensing apparatus for use in biological or chemical assays comprising:

at least one rod having a radius ranging from approximately 2 mm–1 μm and having a wetting tip and at least one non-wetting side, said at least one rod having a diameter less than or equal to the capillary length of said liquid and composed of either a glass, a ceramic, or a polymer material, a support structure holding said at least one rod, and whereby said at least one rod delivers a sub-microliter volume of liquid to a receiving medium.

* * * * *